United States Patent [19]

Grate

[11] Patent Number: 4,992,244
[45] Date of Patent: Feb. 12, 1991

[54] FILMS OF DITHIOLENE COMPLEXES IN GAS-DETECTING MICROSENSORS

[75] Inventor: Jay W. Grate, Alexandria, Va.

[73] Assignee: The United States of America as represented by the Secretary of the Navy, Washington, D.C.

[21] Appl. No.: 250,004

[22] Filed: Sep. 27, 1988

[51] Int. Cl.$^5$ .......................................... G01N 27/04
[52] U.S. Cl. ....................................... 422/98; 422/90; 338/34; 340/633; 340/634
[58] Field of Search ..................... 422/98, 90; 549/3; 338/34; 340/633, 634; 427/51

[56] References Cited

U.S. PATENT DOCUMENTS

| | | | |
|---|---|---|---|
| H477 | 6/1988 | Barger et al. | 540/140 |
| 3,875,199 | 4/1975 | Bloom | 260/429 R |
| 4,062,867 | 12/1977 | Bloom | 260/329 |
| 4,111,857 | 9/1978 | Engler et al. | 528/226 |
| 4,324,761 | 4/1982 | Harris | 422/98 |
| 4,350,660 | 9/1982 | Robinson et al. | 422/90 |
| 4,481,499 | 11/1984 | Arima et al. | 422/98 |
| 4,626,586 | 12/1986 | Wudl et al. | 528/374 |
| 4,636,767 | 1/1987 | Barger et al. | 338/34 |
| 4,654,624 | 3/1987 | Hagan et al. | 422/98 |
| 4,675,423 | 6/1987 | Schrott et al. | 556/136 |
| 4,722,905 | 2/1988 | Honeybourne et al. | 422/98 |
| 4,740,396 | 4/1988 | Uekita et al. | 427/434.3 |
| 4,892,834 | 1/1990 | Rauh | 422/98 |

OTHER PUBLICATIONS

Surface Acoustic Wave Sensors, Chemiresistors and Hybrids Using Both Techniques Simultaneously to Detect Vapors–Barger et al., Proceeding of the Electrochemical Society, vol. 87–15.

Final Report of Microsensor Coating Workshop, Kitritzk, Jarvis, co-chairmen, held Mar. 6–7, 1986, University of Florida.

Primary Examiner—Robert J. Hill, Jr.
Assistant Examiner—Laura E. Collins
Attorney, Agent, or Firm—Thomas E. McDonnell; Barry A. Edelberg

[57] ABSTRACT

Chemical microsensors are fabricated by applying dithiolene transition metal complexes as thin films to chemiresistor devices using the Langmuir-Blodgett technique. The thin films interact with ambient gases and change electrical conductivity upon exposure to a particular gas or vapor. The film material determines the chemical sensitivity and selectivity. The degree of current change depends on the particular gas or vapor and its concentration. These compounds are different in structure and electrical conductive response to gas or vapors than previous materials used for chemical microsensors. This invention is particularly suited for hydrazine detection.

15 Claims, 5 Drawing Sheets

FIG. 5

Testing Sequence and Results for Exposures[a] of BDN Coated Sensors to Hydrazine, Ammonia, Water, MMH and UDMH

| Gas | ppm | Day | 5LB LAYERS Picoamps[b] Baseline[c] | 5LB LAYERS Picoamps[b] Response | 11LB LAYERS Picoamps Baseline | 11LB LAYERS Picoamps Response | 33LB LAYERS Picoamps Baseline | 33LB LAYERS Picoamps Response |
|---|---|---|---|---|---|---|---|---|
| $N_2H_4$ | .5[d] | 0 | .09 | 66[e] | .67 | 670[e] | 5.7 | 4500[e] |
| " | .5 | 0 | | 86 | | 970 | | 7200 |
| " | .5 | 4 | .25 | 140 | 5.8 | 1100 | 74 | 6800 |
| " | 1.0 | 5 | 1.2 | 190 | 20 | 1500 | 390 | 9000 |
| " | .2 | 6 | 1.2 | 26 | 17 | 250[f] | 320 | 1700[f] |
| " | .4 | 7 | 1.1 | 43 | 17 | 420 | 410 | 2700[f] |
| " | 1.4g | 14 | .18 | 94 | 3.0 | 960 | 58 | 5800 |
| " | .5g | 17 | .46 | 14 | 8.8 | 160[f] | 99 | 1100[f] |
| " | 29[d] | 22 | .17 | .81[e] | 3.3 | 14[e] | 71 | 170[e] |
| $NH_3$ | 29 | 22 | .26 | .91 | 6.7 | 16 | 110 | 210 |
| $H_2O$ | 60%RH[d] | 23 | .12 | 1.8 | 2.6 | 14 | 59 | 120[e] |
| " | 60%RH[d] | 23 | .12 | 1.7 | 2.6 | 11 | 67 | 110[e] |
| $N_2H_4$ | .5 | 24 | .13 | 41 | 3.0 | 480 | 76 | 3700 |
| MMH | .5[h] | 29 | .26 | 5.2 | 6.0 | 130 | 79 | 1400 |
| " | .5[h] | 31 | .24 | 4.5 | 13. | 121 | 170 | 1300 |
| UDMH | .5[h] | 34 | .31 | .67 | 9.0 | 18 | 119 | 220 | a Typically 3-4 hour exposures to determine equilibrium responses, exceptions noted.
b 1 volt bias potential applied
c Baselines determined from either an IV curve measurement or current data collected just prior to exposure.
d Response determined from the second of two twenty minute exposures.
e Not a maximum equilibrium response.
f Nearly, but not quite equilibrium.
g Concentrations in some doubt due to erratic hydrazine generator behavior during this testing period.
h Long exposure overnight

FILMS OF DITHIOLENE COMPLEXES IN GAS-DETECTING MICROSENSORS

BACKGROUND OF THE INVENTION

1. Field of Invention

This invention relates to the detection of gases and vapors by microsensors. More specifically, this invention relates to microsensors having a film of a dithiolene transition metal complex which changes detectable physical properties upon exposure to particular gases and vapors.

2. Description of the Prior Art

A chemical microsensor for detecting gases or vapors is composed of a microelectronic device and a chemically sensitive film coated onto the device. The chemical coating determines the sensitivity and selectivity of the sensor. The film undergoes a change in a physical property upon exposure to a vapor or gas to which it is sensitive, and the microelectronic device detects this change. One type of chemical microsensor is the chemiresistor. One type of compound used to make films for a chemiresistor is phthalocyanine compounds.

A chemiresistor exhibits the electrical characteristics of a resistor which has its conductance changed by the presence or absence of some chemical species. Variations in the current flow signal the presence of specific vapors or classes of vapors.

U.S. Pat. No. 4,350,660 discloses that semiconductors have characteristic electronic conductivities which are strongly affected by ambient chemical vapors. U.S. Pat. No. 4,636,767 discusses investigations made on heated metal oxide semiconductors, such as tin oxide and zinc oxide for use in chemiresistors. These semiconductors have not proven to detect vapors very selectively or at concentrations below a few parts per million. U.S. Pat. No. 4,636,767 teaches the use of organic semiconductor films of phthalocyanine compounds as an alternative to heated metal oxides.

Films formed by sublimation or evaporation exhibit slow responses to vapor concentration changes. U.S. Pat. No. 4,636,767 and U.S. Statutory Invention Registration No. H477 teach the Langmuir-Blodgett technique to form semiconducting thin films of phthalocyanine compounds with gas sensing properties.

The film material is the critical component of the sensor since it determines the sensitivity and the specificity for a particular vapor. The remainder of the sensor can be designed to fit the requirements of the material. For example, if the vapor sensitive material is a weakly conducting organic semiconductor, then the device is fabricated with a large number of electrode fingers in an interdigitated array which provides a short electrode spacing with a large electrode perimeter. This arrangement facilitates the measurement of weak currents through resistive materials.

Neutral dithiolene transition metal complexes (dithiene complexes) have been demonstrated to be electronic conductors (Rosa, E. J., Schrauzer, G. N., *J. Phys. Chem.*, 1969, Vol. 73, p. 3132–3138). They have been used as Q-switch dyes for lasers (East German Patent No. 210416, 1984; "New Dithiene Complexes for Q-Switching and Mode-Locking Infrared Lasers", *J. Appl. Phys.*, Vol. 46, No. 11, p. 4852-3, 1975; Japanese Patent No. 80/585881), as an infrared absorbing material (Japanese Patent No. 86/80106) and as a component of optical recording media (Japanese Patent No. 84/78341). These references do not suggest that the compounds could be used in chemical detection. Nor do these references suggest that the compounds would form stable compressed films on the Langmuir-Blodgett film balance or that they could be applied in thin films by the Langmuir-Blodgett technique. Dithiolenes do not possess the structural features of the materials typically used in Langmuir-Blodgett studies, i.e., long alkyl chains.

In many analytical environments, a single sensor is not sufficient to discriminate between the analyte of interest and the other components of the sample. Several sensors in conjunction with pattern recognition techniques are necessary. In order for pattern recognition techniques to be effective, the individual sensors must have different response patterns to the ambient vapors. To achieve this result, the materials coated onto each of the individual sensors must be different from one another. For this reason, it is important that as many different materials as possible be developed for gas sensing.

SUMMARY OF THE INVENTION

It is an object of this invention to detect minute quantities of chemical vapors and gases.

Also, it is an object of this invention to detect toxic gases in military environments, such as ships, jet cockpits, ground installations, battlefields and space vehicle launch sites.

Further, it is an object of this invention to detect low concentrations of hydrazine.

Finally, it is an object of this invention to have a sensor which is reusable after exposure to a regenerative media.

These and other objects are accomplished by a chemical microsensor containing a film of a dithiolene transition metal complex in which a measurable physical property changes upon exposure to a particular chemical vapor.

BRIEF DESCRIPTION OF THE DRAWINGS

FIG. 5 is a table of the response of sensors with varying number of Langmuir-Blodgett layers to hydrazine, ammonia, water, monomethylhydrazine (MMH) and 1,1-dimethylhydrazine (UDMH).

DETAILED DESCRIPTION OF THE INVENTION

This invention provides an apparatus for detection of chemical gases and vapors by measuring the effect of the gases and vapors on the physical properties of a film deposited on a microelectronic device. The effect of the gases and vapors on the film causes the physical properties of the film, such as conductivity and mass, to change. This change is measured by the electronic device, such as a chemiresistor sensor or a surface acoustic wave device.

Figure 1:
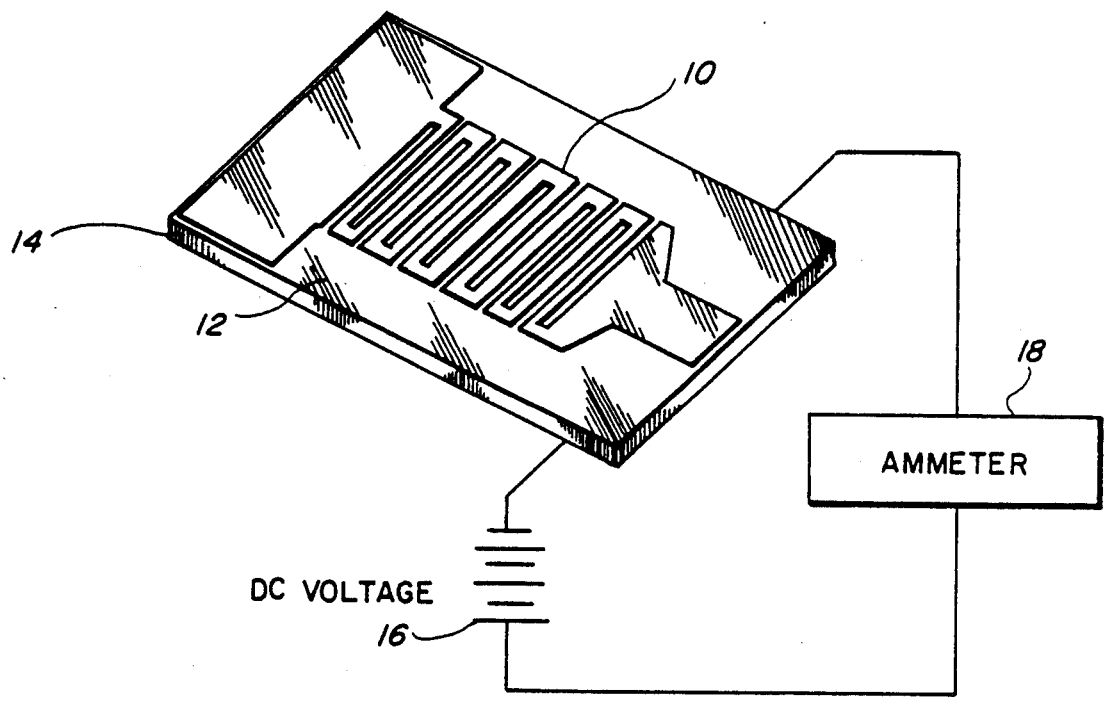
FIG. 1 is a schematic diagram of a typical chemiresistor sensor.
Figure 1A:
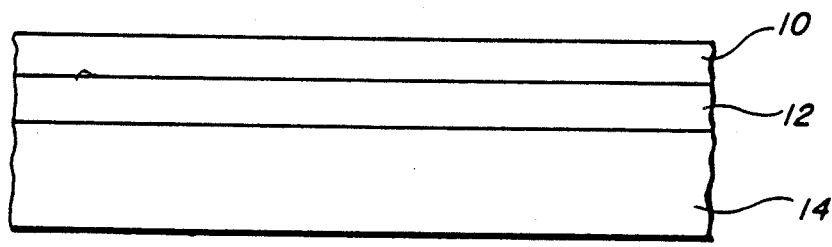
FIG. 1a is a detail of the schematic diagram of a chemiresistor sensor.

In a typical chemiresistor such as is shown in FIGS. 1 and 1a, a film 10 is deposited onto an interdigitated electrodes 12 on a substrate 14. The film is electrically conductive and changes conductivity when exposed to an chemical gas or vapor of analytical interest. The interdigitated electrodes are of a conductive material, such as gold. The substrate is of an insulating material, such as quartz. A potential is applied by power supply 16 and the resulting current flow is measured by a current measuring device 18.

In order for a material to be used as a film 10 in FIG. 1 in a chemiresistor sensor, it must be suitable for making a thin film on the interdigitated electrodes, conduct an electrical current when applied as a thin film on the interdigitated electrodes, and undergo a change in its electrical conductivity upon exposure to a chemical gas vapor of interest. In addition to these physical properties, the film material must be compatible with the processing technique used to make the film coating. Coating the film on the microelectronic device is done by any of the known methods of coating films, such as the Langmuir-Blodgett technique, spin-coating, spray-coating, sublimation or vacuum evaporation. The Langmuir-Blodgett technique is preferred for applying very thin films.

In order for a material to be suitable for application to a surface by the Langmuir-Blodgett technique, it must be extremely insoluble in the water subphase, even when a surface film of the material is compressed, be soluble in an organic solvent, so that it can be spread on the surface, form a surface film which can be pressurized without collapse at the pressures needed to transfer it to a substrate, and transfer to the substrate when the substrate is passed through the surface film. Long chain fatty acids are typical of the material used in the Langmuir-Blodgett technique.

Figure 2:
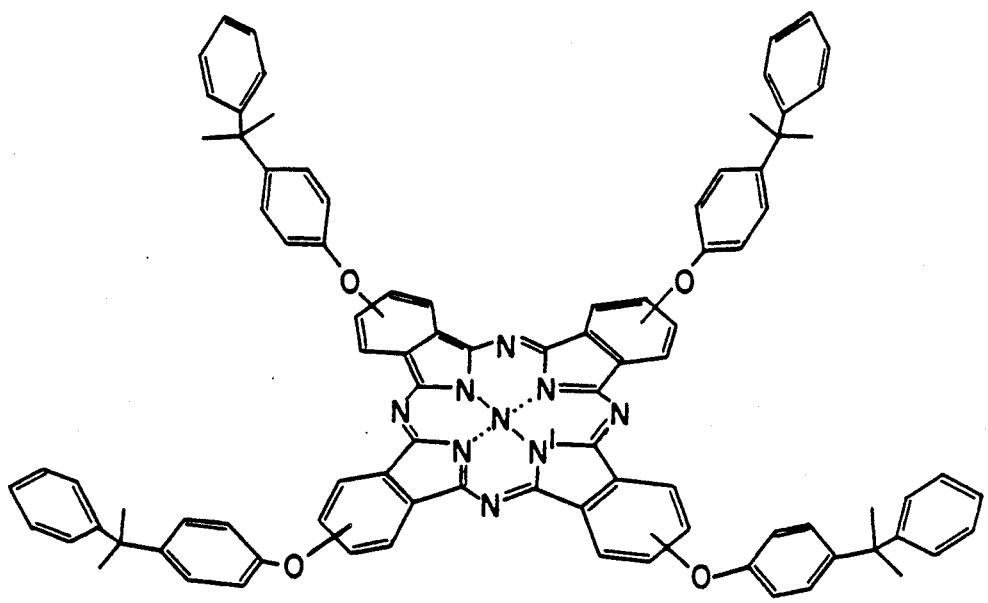
FIGS. 2 and 2a are diagrams of the structures of a dithiolene transition metal complex and a phthalocyanine compound.
Figure 2A:
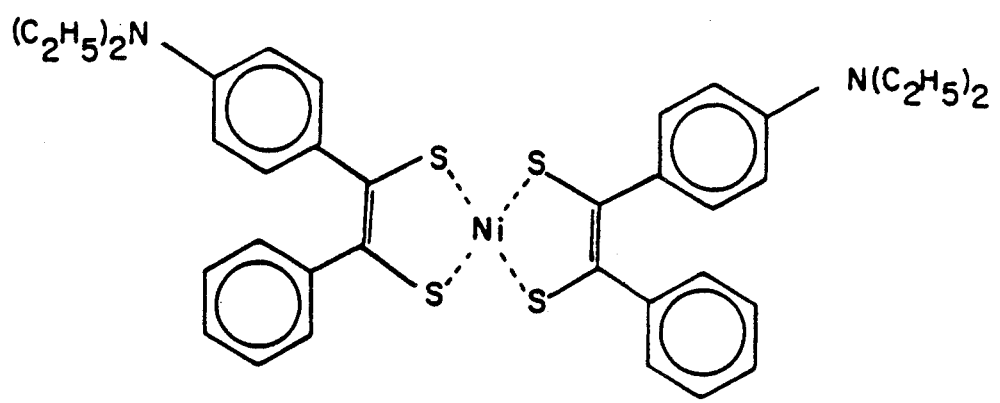

The dithiolene complexes are not typical of compounds used in the Langmuir-Blodgett technique and are different from the compounds typically used as coatings on chemiresistor sensors, such as phthalocyanine compounds. The dithiolene complexes and the phthalocyanine compounds are structurally different (FIGS. 2 and 2a). They also conduct electricity differently. Phthalocyanines are p-type semiconductors, whereas the dithiolenes are n-type semiconductors. Upon exposure to hydrazine, which is a reducing agent, the conductivity of phthalocyanine-containing Langmuir-Blodgett films is reduced to levels where it cannot be accurately measured above background leakage currents and noise. Concentrations of hydrazine cannot be measured with such a device. By contrast, the conductivity of the dithiolene-containing films increase dramatically upon exposure to hydrazine. The signals are easily measured and have high signal-to-noise ratios.

Dithiolene complexes contain cis-1,2-disubstituted ethylene-1,2-dithiolate anions as ligands. These ligands form 5-membered unsaturated chelate rings in metal complexes as shown

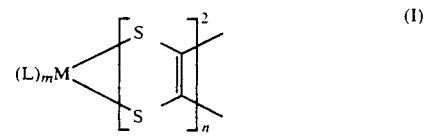

where the dithiolene ligand is within the brackets, n is 1, 2 or 3, L is another ligand, m is 0, 1 or 2 and M is the metal atom and z, the charge on the complex, is typically 0, −1 or −2. Bis(dithiolene) metal complexes are electrically conductive and can be used as the chemically sensitive material in a chemical sensor. The preferred embodiment of this invention includes all metal bis(dithiolenes) as shown below:

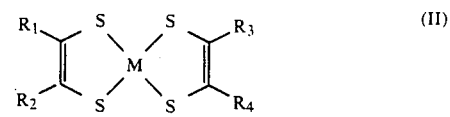

wherein M is a divalent metal, and $R_1$, $R_2$, $R_3$ and $R_4$ end groups are hydrogen, alkyls, aryls, substituted alkyls or substituted aryls. The choice of end groups can affect physical properties of the compound, such as electrical conductivity, solubility, heat resistance, durability and the ability to form a Langmuir-Blodgett film. Preferable compounds have as the divalent metal nickel, palladium, platinum, copper, zinc, gold, iron or cobalt and have as the end groups hydrogen, an alkyl with 20 carbons atoms or less, an aryl, such as phenyl, or an aryl, such as phenyl, substituted with an alkyl, an alkoxy or a tertiary amino group. The most preferred divalent metal is nickel and the most preferred end groups are selected from the group of aryls, such as diethylaminophenyl. The charge on the complex can be 0, −1 or −2.

Tris(dithiolene) metal complexes are also electrically conductive and can be used in a chemical sensor. The structure of a tris(dithiolene) complex is shown below:

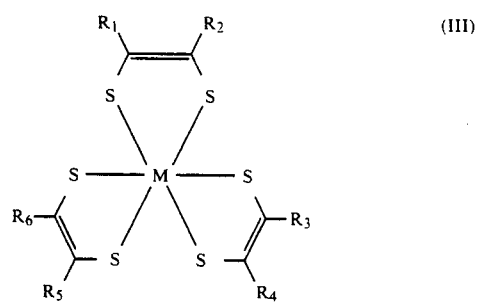

wherein M is a trivalent metal, and $R_1$, $R_2$, $R_3$, $R_4$, $R_5$ and $R_6$ are hydrogen, alkyls, aryls, substituted alkyls or substituted aryls. Preferable compounds have as the trivalent metal iron or cobalt and have as the end groups hydrogen, an alkyl with 20 carbons atoms or less, an aryl such as phenyl, or an aryl such as phenyl substituted with an alkyl, an alkoxy or a tertiary amino group.

Polymeric materials which contain bis(dithiolene) metal units in the chain with repeating unit of the structure shown below are alternate material for film in this invention.

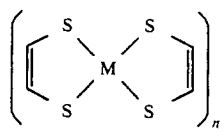

wherein M is a divalent metal, and n is the number of repeating units of any integer greater to or equal to one. Preferable compounds have as the divalent metal nickel, palladium, copper or platinum. These polymeric materials can be prepared by replacing the dithiolate ligand as shown in (I) above with a tetrathiolate, such as ethylenetetrathiolate, tetrathiosquarate or tetrathiofulvalenetetrathiolate, structures of which are shown below:

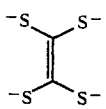

ethylenetetrathiolate

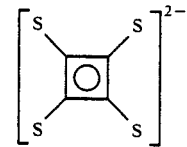

tetrathiosquarate

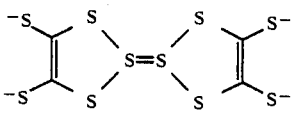

tetrathiofulvalenetetrathiolate

Evaluation of a dithiolene compound in a chemiresistor demonstrated that it would form a film by the Langmuir-Blodgett technique that conducts electricity sufficiently such that the changes in conductivity upon exposure to low concentrations of gases and vapors would be measurable. Bis(4-diethylaminodithiobenzil)nickel in combination with stearyl alcohol was applied as a thin film to a chemiresistor by the Langmuir-Blodgett technique and exposed to vapors. Observable changes in current flow were noted upon exposure to water, ammonia, nitrogen dioxide, sulfur dioxide, dimethylmethylphosphonate, diethylsulfide, hydrazine and hydrazine derivatives.

Dithiolene complexes of transition metals can be applied to chemiresistor devices by vacuum evaporation, sublimation or the Langmuir-Blodgett technique. Vacuum sublimation and vacuum deposition of some of these compounds has been disclosed in other references. Generally, dithiolene complexes are applied to chemiresistor devices by vacuum evaporation or sublimation in the range from about 0.5 to about 5 microns. Thickness for a Langmuir-Blodgett film used in a chemical sensor in this invention is in the range from about 25 Angstroms to about 1 micron.

Films of Bis(4-diethylaminodithiobenzil)nickel are more easily transferred from the Langmuir-Blodgett trough to the chemiresistor device when the film also contains an amphiphilic molecule, such as stearyl alcohol. In this context, the stearyl alcohol is a transfer promoter. Other amphiphilic molecules or water-insoluble polymers can be used in combination with the dithiolene complex to prepare thin films on sensor devices.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Triply distilled water was used as the subphase in a Langmuir-Blodgett trough. The trough was paraffin-coated and controlled by a thermostat. A 1:1 mole ratio solution of bis(4-diethylaminodithiobenzil)nickel (indexed name Nickel, bis[1-[4-(diethylamino)phenyl]-2-phenyl-1,2-ethenedithiolato(2-)-S,S'] and registry numbers 51449-18-4 and 90242-58-3, referred to as BDN) and stearyl alcohol was prepared in chloroform. Five tenths mL of this solution having a concentration of 0.5 mg/mL of the BDN complex was spread on the distilled water to form a surface film. Surface tension measurements were made with a strain gage. The surface film was compressed to a film pressure on 20 dynes/cm by a bar controlled by a microcomputer to produce an average area per molecule of 15 square angstroms.

The chemiresistor devices to which film were applied consisted of one or more pairs of gold interdigitated electrodes microfabricated in a pattern onto a quartz surface. The film transfer operation began with the substrate submerged. The device was coated and allowed to air dry for 5 minutes after each dip. The dipping velocity was $4.4 \times 10^{-4}$ m/sec. Sensors were prepared with 1, 5, 11, 21, 33 and 45 layers deposited on the device. The film contained stearyl alcohol in addition to the dithiolene complex. The resistance of each sensor was determined by placing it in a controlled atmosphere (typically dry air) and measuring the current in the dark while applying a voltage across the interdigitated electrodes from 0 to $+1.25$ volts, down to $-1.25$ volts and back up to 0 volts by 0.05 volt steps.

The response of each sensor to the gases and vapors was determined by measuring the current through the sensor with an autoranging programmable electrometer while a constant bias voltage of one volt was applied across the interdigitated electrodes. The sensors were contained in a chamber through which a carrier gas (typically dry air) was flowing at 200 mL/min. A calibrated concentration of test vapor was added to the carrier gas. In individual experiments, the sensor being tested was exposed to a carrier gas containing a calibrated concentration of water at 5000 to 19,000 ppm, ammonia at 10 to 100 ppm, nitrogen dioxide at 5 to 10 ppm, sulfur dioxide at 0.2 to 2 ppm, dimethylmethylphosphonate at 1 to 10 ppm, diethyl sulfide at 2000 to 20,000 ppm, hydrazine at 0.2 to 1.4 ppm or hydrazine derivatives at 0.5 ppm. Of the six sensors with a different number of layers (1, 5, 11, 21, 33 and 45), only the sensor with one layer did not respond to the gases.

EXAMPLE II

Figure 3:
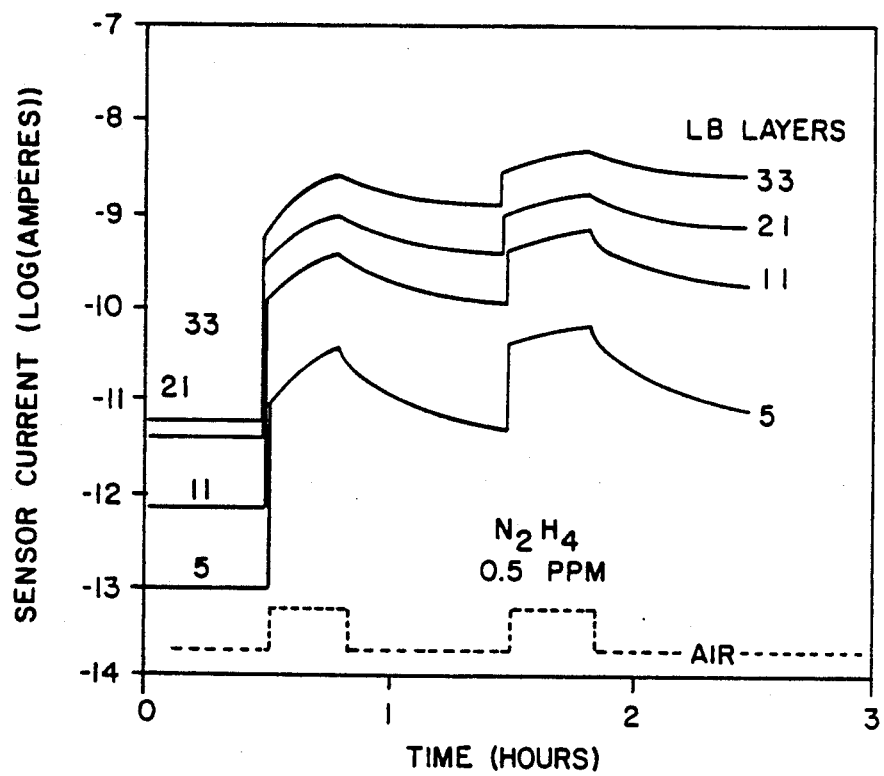
FIG. 3 is a plot of the responses of sensors with varying number of Langmuir-Blodgett layers to hydrazine.

Five sensors of 1, 5, 11, 21 and 33 layers prepared as in Example I were tested simultaneously in a gas-exposure chamber. The experiment began by following the baseline current under dry air for 30 minutes. Dry air containing 0.5 ppm of hydrazine was introduced for 20 minutes followed by clean air for 40 minutes, hydrazine again for 20 minutes and clean air for another 40 minutes. The currents observed are shown in FIG. 3. Exposure to hydrazine produced a two order of magnitude increase in current within two minutes. As shown in FIG. 3, the sensors with the fewest layers had an initial recovery that was faster than those with more layers.

EXAMPLE III

Figure 4:
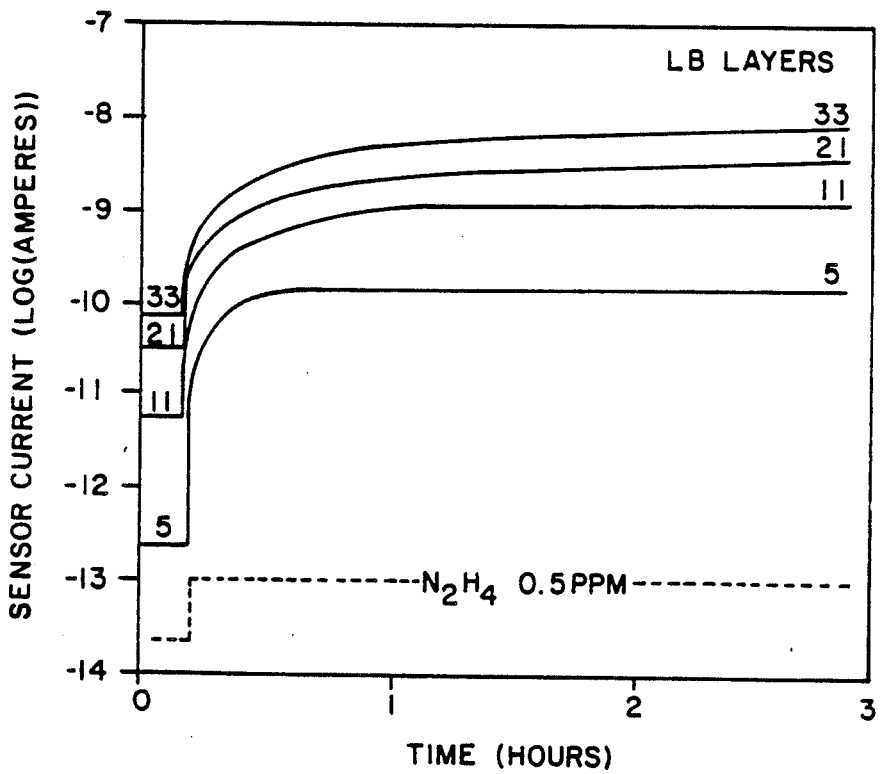
FIG. 4 is a plot of the responses of sensors with varying number of Langmuir-Blodgett layers to hydrazine after continuous exposure and recovery.

After the experiment in Example II, the sensors were exposed to a continuous hydrazine concentration of 0.5 ppm for 3 hours in order to determine the steady state response current level. The 5-layer sensor was the fastest to respond, requiring about 1 hour to reach equilibrium level. The sensors were allowed to recover for four days under dry air. Only the 5-layer sensor recovered to near baseline current level prior to any hydrazine exposure. The three hour continuous hydrazine exposure was repeated to demonstrate that the steady state response current levels were reproducible. These results are shown in FIG. 4.

EXAMPLE IV

Figure 6:
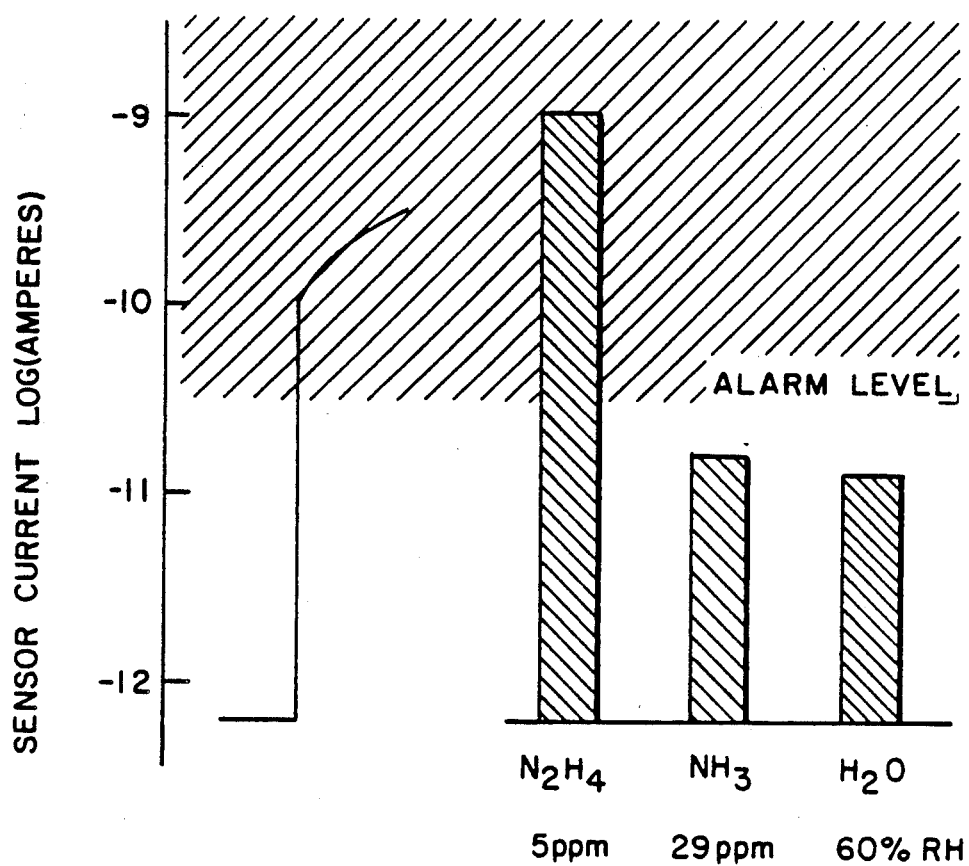
FIG. 6 is a representation of the response of the sensor current to hydrazine, ammonia and water vapor.

Sensors of 5, 11, 21 and 33 layers prepared as in Example I were exposed to ammonia at 29 ppm. The current increased by 10–20 fold, but response time was slow, requiring three hours to reach equilibrium. Response levels of the sensors were 100 to 33 times less than the responses to 0.5 ppm hydrazine, as shown in FIG. 5. Results, as shown in FIG. 6, demonstrate the response level of the dithiolene film is such that detection of hydrazine would not be obscured by the presence of ammonia.

EXAMPLE V

Sensors of 5, 11, 21 and 33 layers prepared as in Example I were exposed to 60% relative humidity at room temperature (roughly equivalent to 19,000 ppm). The response level of the sensors was similar to those of 29 ppm ammonia, 60 to 70 times less than those for 0.5 hydrazine, as shown in FIG. 5. Results, as shown in FIG. 6, demonstrate the response level of the dithiolene film is such that detection of hydrazine would not be obscured by the presence of water vapor.

EXAMPLE VI

Sensors of 5, 11, 21 and 33 layers prepared as in Example I were exposed to 0.5 ppm monomethylhydrazine (MMH) and 0.5 ppm 1,1-dimethylhydrazine (UDMH). The response levels of the sensors were similar to those for 29 ppm of ammonia and 19000 ppm of water as shown in FIG. 5. Responses to MMH were approximately seven times higher than those to UDMH but still less than those to hydrazine.

As shown in examples above, chemiresistors using films of dithiolene complex material are extremely sensitive to hydrazine. Responses to concentrations as low as 200 ppb have been shown. Projections based on signal and noise levels at this level indicate that a sensor exposed to 1 ppb hydrazine in clean dry air would give a measurable signal.

These sensors can be used in alarm devices for hydrazine leaks. The American Conference of Governmental Industrial Hygienist has set a threshold limit value for hydrazine of 100 ppb. NIOSH has recommended a value of 30 ppb. Both are detectable by these sensors.

As shown in the examples above, a one-layer Langmuir-Blodgett film of BDN was not responsive to the chemical vapors. A plurality of Langmuir-Blodgett layers of BDN was required to form a film which had its conductivity observably changed upon exposure to chemical vapors. The number of Langmuir-Blodgett layers depends on the particular application and the material used for the film coating. Fewer layers respond and recover faster, but more layers can give better signal to noise. The preferred embodiment would have 3 to 33 layers.

Sensors can be prepared having Langmuir-Blodgett films of greater or fewer than the 5 to 45 layers which were successfully evaluated using BDN. A sensor having a film of only one layer will be functional if there is an increased proportion of the dithiolene complex in the film. Replacing the combination of dithiolene complex and stearyl alcohol with pure dithiolene complex material in the Langmuir-Blodgett process increases the likelihood of forming a functional one-layer sensor because of the increased content of dithiolene material in the layer. The same would be true if only a lesser amount of the transfer promoter were used with the dithiolene complex.

Another type of chemical sensors prepared by applying films of dithiolene is a surface acoustic wave (SAW) device. The film is deposited by the Langmuir-Blodgett technique or any other known method of coating films. The SAW device responds to the changes in mass and electrical conductivity which occur when the film absorbs the gas or vapor to which the film is sensitive.

Obviously, additional modifications and variations of the present invention are possible in light of the above teaching. It is therefore to be understood that within the scope of the appended claims the invention may be practiced otherwise than as specifically described herein.

What is claimed and desired to be secured by Letters Patent of the United States is:

1. A chemical microsensor for detection of gases and vapors, comprising:
   a. an insulating substrate;
   b. a film comprising a dithiolene complex of a transition metal covering the substrate wherein a measurable physical property of the film changes upon exposure to gases and vapors;
   c. a sensing element to detect any change in physical properties of the film.

2. A chemical microsensor as recited in claim 1 wherein the film comprises a bis(dithiolene) complex of the following formula:

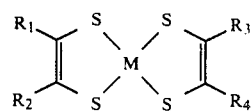

wherein M is a divalent metal and R1, R2, R3 and R4 are chosen from the group consisting of hydrogen, alkyl, aryl, a substituted alkyl and a substituted aryl.

3. A chemical microsensor as recited in claim 1 wherein the film comprises a tris(dithiolene) complex of a transition metal of the following formula:

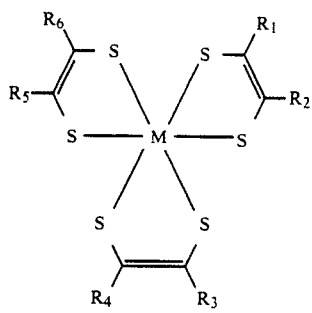

wherein M is a trivalent metal and R1, R2, R3, R4, R5 and R6 are chosen from the group consisting of hydrogen, alkyl, aryl, a substituted alkyl and a substituted aryl.

4. A chemical microsensor as recited in claim 1 wherein the film comprises a polymer with the repeating unit of the formula:

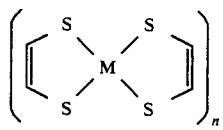

wherein M is a divalent metal and n is an integer greater than one.

5. A chemical microsensor comprising
a. a substrate of insulating material;
b. a conductive material microfabricated in a pattern on the substrate; and
c. a film covering the substrate and the conductive material wherein the electrical conductivity of the film changes upon exposure to gases and vapors and wherein the film is a bis(dithiolene) complex of a transition metal of the following formula:

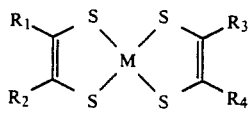

wherein M is a divalent metal and R1, R2, R3 and R4 are chosen from the group consisting of hydrogen, alkyl, aryl, a substituted alkyl and a substituted aryl;
d. a sensing element to detect any change in electrical conductivity.

6. A chemiresistor for detection of gases and vapors chosen from the group consisting of water, ammonia, nitrogen dioxide, sulfur dioxide, dimethylmethylphosphonate, diethylsulfide, hydrazine and substituted hydrazine compounds in which the electrical conductivity changes upon exposure to the gases and vapors, comprising:
a. a substrate of insulating material;
b. a conductive material microfabricated in a pattern on the substrate; and
c. a film covering the conductive material wherein the electrical conductivity of the film changes upon exposure to gases and vapors and wherein the film comprises a bis(dithiolene) complex of a transition metal of the following formula:

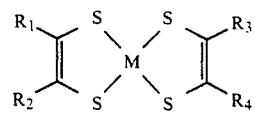

wherein M is a divalent metal and R1, R2, R3 and R4 are chosen from the group consisting of hydrogen, alkyl, aryl, a substituted alkyl and a substituted aryl;
d. a sensing element to detect any change in electrical conductivity.

7. A chemiresistor as recited in claim 6 wherein the film is 0.5 to 5 micron thick.

8. A chemiresistor as recited in claim 6 wherein the divalent metal is chosen from the group consisting of nickel, palladium, and platinum.

9. A chemiresistor as recited in claim 8 wherein $R_1$–$R_4$ are chosen from the group consisting of hydrogen, an alkyl with 20 carbons atoms or less, an aryl, or an aryl, substituted with an alkyl, an alkoxy or a tertiary amino group.

10. A chemiresistor as recited in claim 9 wherein the film comprises bis(diethylaminodithiobenzil)nickel of the following formula:

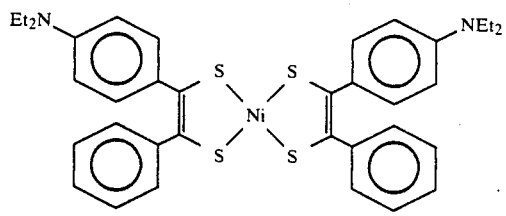

11. A chemiresistor as recited in claim 10 wherein the film is a film in the range of three to thirty-three layers.

12. A chemiresistor as recited in claim 11 wherein the film is a film of five layers.

13. A chemiresistor as recited in claim 12 wherein the substrate is quartz.

14. A chemiresistor as recited in claim 13 wherein the conductive material comprises at least one pair of gold interdigitated electrodes.

15. A surface acoustic wave device for detection of gases and vapors, comprising:
a. a substrate;
b. a film covering the substrate wherein the mass and/or electrical conductivity of the film changes upon exposure to gases and vapors resulting in a detectable change in frequency and wherein the film is a bis(dithiolene) complex of a transition metal of the following formula:

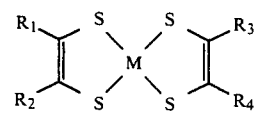

wherein M is a divalent metal and R1, R2, R3 and R4 are chosen from the group consisting of hydrogen, alkyl, aryl, a substituted alkyl and a substituted aryl.
d. a sensing element to detect any change in electrical conductivity and mass.

* * * * *